United States Patent [19]
Damavarapu et al.

[11] Patent Number: 5,977,418
[45] Date of Patent: Nov. 2, 1999

[54] REGIOSELECTIVE NITRATION OF AROMATIC COMPOUNDS BY DINITROGEN PENTOXIDE AND THE REACTION PRODUCTS THEREOF

[76] Inventors: Reddy Damavarapu, 13 Riva Dr., Hackettstown, N.J. 07840; Keerthi Jayasuriya, 56 Sparrow Cir., Newton, N.J. 07860; Thomas J. Kwok, 500 Sioux Ave., Parsippany, N.J. 07034

[21] Appl. No.: 09/009,633

[22] Filed: Jan. 20, 1998

[51] Int. Cl.$^6$ .................................................. C07C 205/00
[52] U.S. Cl. ........................................... 568/927; 568/936
[58] Field of Search ..................................... 568/927, 936

[56] References Cited

PUBLICATIONS

Jounal of Organic Chemistry, 1994, (59), pp. 4939–4942, Thomas J. Kwok et al.

Japanese abstract (JP 51019734), Feb. 17, 1976, Tokeo et al.

Journal of Pharmaceutical Science, 1988, 77 (2), pp. 185–187, Gaudreaut.

Journal of Chem. Soc., Chem. Commun. (1994), (12), pp. 1443–1444, Hitomi et al.

*Primary Examiner*—Paul J. Killos
*Assistant Examiner*—J. Parsa

[57] ABSTRACT

The invention is a process for regioselective nitration of substituted aromatic compounds and the corresponding reaction products. The reaction is conducted in the presence of a solid zeolite with small pores and with nitrogen pentoxide as the nitrating agent. The reaction products have a very high proportion of para-nitro substituted isomer.

12 Claims, No Drawings

REGIOSELECTIVE NITRATION OF AROMATIC COMPOUNDS BY DINITROGEN PENTOXIDE AND THE REACTION PRODUCTS THEREOF

STATEMENT OF GOVERNMENT INTEREST

The United States of America has certain rights and licenses in this invention

SUMMARY OF THE INVENTION

The invention concerns highly selective and directed processes for the nitration of aromatic ring compounds. It concerns effecting such nitrations by using a solid, acidic zeolite of selected pore size and dinitrogen pentoxide, $N_2O_5$, as the nitrating agent. Optionally, the process may be conducted in a solvent for the pentoxide; methylene chloride is one such solvent. The invention includes the processes and the novel product mixtures produced by the processes. The zeolite is a shape selective material having pore sizes to accommodate the aromatic compound. The invention provides mononitrations at para positions of the substituted aromatic compounds and high yields of these desired products.

In general, the process is a nitration of ring activated aromatic compounds with nitrogen pentoxide as the nitrating agent and a solid, small pore size, acidic aluminosilicate zeolite as a catalyst. In particular, it provides a process which tends to produce derivatives of the substituted aromatic compound that will have a nitro substituent at the para position. There is a high selectivity for the production of the para isomer, which will reduce the proportion of ortho isomer. Furthermore, under the conditions of the reaction of this invention, the meta isomer and other byproducts are produced in very small or negligible amounts. It is desirable to reduce these materials to essentially 0%. The reaction product will be predominately the para substituted isomer,; in some circumstances, the product will be essentially 100% para isomer. In some cases, the reaction products having small ortho contents can themselves be used as feedstocks. Also, the composition of the reaction products is such that it lends itself to further separations into its individual components.

One particular application of the invention is the regioselective nitration of substituted aromatic hydrocarbons such as toluene to mononitrotoluenes. Another particular application of the invention is the regioselective nitration of substituted aromatic compounds in which the substituent is an electron withdrawing group which uses mesomerism with the aromatic ring to activate the ring and establish ortho and para directed sites. Exemplary electron-withdrawing groups of this type are ethers and halogens. Preferred examples of compounds that are suitable for nitration in this process are anisole and chlorobenzene.

The invention includes the novel reaction products which have a major proportion of para isomer and a minor proportion of ortho isomer; the proportion of para isomer in the product may be at least about 80% by wt. and up to essentially 100%. A particular class of compounds of interest are para-nitro aromatic compounds that are intermediates for pharmaceuticals. The aromatic ring product compounds may be substituted with other groups in addition to the ring activating group and its para nitro group.

The invention includes novel separation techniques for such reaction products and the use of these reaction products as feedstocks in other chemical processes. For example, mononitrotoluenes produced by the invention can be nitrated by other conventional processes to dinitrotoluenes: in turn, the dinitrotoluenes can be nitrated to trinitrotoluene. The nitro anisole may be reduced to its corresponding amine for use as an intermediate in the preparation of pharmaceuticals and dyestuffs. The same can be done with the nitrochlorobenzene.

FIELD OF THE INVENTION

Nitration reactions of substituted aromatic compounds are important for the industrial production of a wide variety of essential chemical intermediates, high value commercial compounds such as p-nitrochlorobenzene and end products, including high energy explosives such as 2,4,6-trinitrotoluene (TNT). For the nitration of aromatic hydrocarbons, especially toluene, the most widely used nitrating agents are mixtures of concentrated HN03 and H2SO4 as described by Olah, Malhotra and Narang, "Nitrations", VCH Publications, New York, (1989) at page 5. These nitration reactions are conducted under homogeneous conditions which are very corrosive and which involve serious environmental problems in the methods and costs of disposal of the spent mixed acids. These reactions also have the problem of poor distribution of isomers in the reaction products. A variety of systems have been attempted for the nitration of toluene. Smith has reported (Smith, K.; Fry, K, Tetrahedron Lett., 1989, 30, 5333) a nitration of toluene which uses large pore-size mordenite catalyst and benzoyl nitrate as the nitration source. The reaction product has a controlled distribution of isomers. There are problems in this process with the making and handling of benzoyl nitrate. There is a strong tendency toward decomposition in moisture and air. In addition, the benzoic acid by-product requires removal with caustic aqueous extraction. Lazlo has reported (Cornelis, A.; Delaude, L.; Gerstmans, A.; Laszlo, P., Tetrahedron Lett., 1988, 29, 5657) a nitration of toluene which uses using a clay catalyst, $Cu(NO_3)_2$ and acetic anhydride. The reaction product has about 1% meta isomer. To achieve such selectivity requires high dilution of reagents, such as 1 ml of toluene in 2 liters of $CCl_4$. The high cost of copper nitrate would make large scale-up of the processes impractical. A patent from Russian researchers (USSR, SU 1,759,833, 1992) generally describes a nitration of toluene with a solid zeolite catalyst, ZSM-11, and some form of nitric acid. Kwok et al , (J. Org. Chem., 1994, Vol.59(17), ppgs.4939–4942) describe the nitration of ring activated aromatic compounds such as toluene with a solid, acidic aluminosilicate, zeolite ZSM-5 catalyst of 5 to 5.4 Angstrom pore size and alkyl nitrates as nitrating agents; the high cost of the nitration agent limits the utility of this work to model studies.

DETAILED DESCRIPTION OF THE INVENTION

The present invention concerns the regioselective nitration of substituted aromatic compounds with nitrogen pentoxide as the nitrating agent and a solid, acidic zeolite catalyst of small pore size. The aromatic compound will be substituted with at least one ring activating, ortho and para directing group. The preferred directing groups of the substituted aromatic compounds are members selected from alkyls, substituted alkyls, ethers, acids, oxyacids, alkoxides and halogens. The preferred alkyl groups are methyl, ethyl, propyl or isopropyl. Preferred substituted aromatic compounds are toluene, ethyl benzene and cumene. As discussed previously, the group may be electron withdrawing if it also will form mesomeric bonding with the aromatic ring. The mesomeric bonding causes the ortho and para directing effect in the ring. Examples are oxygenated alkyls and halogens. When the substituents are oxygenated groups, they may be alkoxy or acyloxy. Preferred members of this group are anisole and 4-phenyl butryic acid. When the groups are halogen, the preferred members are chlorine and bromine. The reaction product will have an isomer distribution with a very high para isomer distribution, a small ortho content and a very low meta isomer content. It is preferred to have essentially 100% of the substituted aromatic compound isomers to be in the para form.

The nitration process of this invention is very selective and uses mild conditions. The process features high yields of the para isomer; the ortho isomer will be produced in relatively low amounts and in some cases there will be none. The meta isomer will be in very low even negligible amounts.

The nitrating agent used in the invention is nitrogen pentoxide ($N_2O_5$). It may be prepared in situ when it is needed for the reaction. An example of the preparation is given below. It is prepared in solution and used as a solution in the examples which follow.

The zeolite catalysts used in this invention are synthetic aluminosilicate compounds having a crystalline framework with well defined pore and cage structures. The basic structural units consist of silicon and aluminum atoms that are tetrahedrally coordinated with four oxygen atoms. Each polyhedron has a rigid geometric form and the way these polyhedron forms are connected determines the pore size of the channels in the crystal lattice. In accordance with the present invention, the pore size of the zeolite catalysts should be in the range of 5 to 5.5 A. The pore size and shape selectivity of the zeolite catalyst have been found to play a significant role in controlling the isomer distribution of products in the nitration of substituted aromatic compounds with concentrated nitric acid. It has been observed in ZSM-5 that the para nitro isomer of the substituted compound is formed in more significant amounts as compared with conventional electrophilic nitration methods. By contrast, it appears that the use of larger pore size zeolites or multi-channel, cross network zeolites is ineffective in controlling the isomer distribution, particularly the meta isomer, of the products from the nitration of toluene. The best isomer distribution of mononitrotoluene reaction products is obtained by using a zeolite catalyst such as ZSM-5 having a pore size from about 5 to 5.4 A. Several H-ZSM-5 zeolite materials with different Si/Al ratios have been investigated to determine the most suitable catalyst composition to optimize the desired isomer distribution in the reaction products. The range of Si/Al ratio is from about 120 to about 1000. The use of this catalyst is one factor that controls the isomer distribution to reduce the undesirable meta isomer and increase the desired para-nitrotoluene isomer significantly.

The practice of the invention is illustrated in the following examples. The solid, aluminosilicate H-ZSM-5 zeolite catalyst was in the protonated form, a white powder and had a ratio of $SiO_2/Al_2O_3$, (Si/Al), of 1000 unless otherwise noted below. The materials were obtained from Degussa Corporation, Fort Lee, N.J., and PQ Corporation, Valley Forge, Pa. The catalyst was used in the protonated form in the initial reactions. It was regenerated by calcination in air. Then, it was used in the regenerated form without additional protonation. The catalyst was calcined in air at 550° C. for 4 hours prior to use. The nitration reactions were performed in a round-bottom flask using a Teflon coated magnetic spin bar and in air unless otherwise noted.

The reaction is conducted under heterogeneous conditions. The initial reagents are in the liquid phase with the zeolite catalyst in the solid phase. At the end of the reaction, the solid catalyst is separated from the solution of the reactants and products. The products are recovered from the solution. Generally, the reaction products were slurries of solid para isomer crystals in a liquid phase containing volatile solvent and ortho isomers. The products were separated by fractional distillation into the pure components. The product distribution for each reaction was determined by gas chromatography using a Hewlett-Packard -5890 unit and a packed column 1 m by 0.533 mm capillary column. GC/MS was done with a Saturn 4D Spectrometer. The instruments were calibrated with pure reference samples.

GENERAL METHOD TO MAKE $N_2O_5$

A 25 ml portion of distilled methylene chloride was placed in a 250 ml roundbottom flask fitted with a stopcock and a Teflon coated magnetic spin bar. Nitrogen gas was introduced into the system and flask was cooled to 0° C. After the solution was stirred for 5 minutes, 2 ml (0.048 mol) of 98% nitric acid was added into the flask and stirring continued. After 10 minutes., 6.5 grams of phosphorus pentoxide was added to the solvent/acid mixture and stirring continued for an additional 60 minutes at 0°. The $N_2O_5$ in methylene chloride is a clear and colorless solution when separated from the phosphorus pentoxide mixture. A carefully measured 1–2 ml aliquot of this solution was decomposed in 30–40 ml of deionized water and titrated with standardized sodium hydroxide solution using phenolphthalein as the endpoint indicator. The typical amount of $N_2O_5$ is 0.0004 mol/ml $CH_2Cl_2$ or when scaled up is about 40% yield (0.01–0095 mol.).

EXAMPLE A NITRATION OF TOLUENE USING $N_2O_5$

A mixture of 50 ml of dried toluene and 10 g. of H-ZMS-5 was placed in a three neck 250 ml flask, stirred and heated at 70° C. The $N_2O_5$ (0.010 mol.) and methylene chloride solution was decanted into an addition funnel and added to the heated mixture dropwise over a 10 minute period. The original mixture was light tan and became a orange color as the reaction proceeded. The mixture was stirred for 4 hours and the temperature was kept between 70–75° C. At the conclusion of the experiment, the flask was cooled to touch and the catalyst and solution were separated by filtration through a sintered glass funnel with medium porosity. The volatile components, primarily toluene and methylene chloride, were removed from the filtrate under reduced pressure. The remaining residue is a slurry of well defined crystals that are 0.7 grams of essentially mononitrotoluenes representing a yield of 51% based on 1.1 grams of $N_2O_5$. The ratio of isomers for the mononitrotoluene was 94% para, 6% ortho and a trace amount of (0.19%) meta.

EXAMPLE B NITRATION OF TOLUENE USING $N_2O_5$

A mixture of 50 ml of dried toluene and 10 g. of H-ZSM-5 having a $SiO_2/Al_2O_3$ of 1000 was placed in a three neck 250 ml flask, stirred and heated to 110° C. The $N_2O_5$ (0.009 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 105–115° C. At the conclusion of the experiment the flask was cooled to touch and the catalyst and solution was separated by filtration through a sintered glass funnel with medium porosity. The volatile components, primarily toluene and methylene chloride removed from the filtrate under reduced pressure. The remaining residue is a slurry of well defined crystals that are essentially mononitrotoluenes having an isomer distribution of 95% para, 5% ortho, and trace amounts of meta (0.13%).

EXAMPLE C NITRATION OF TOLUENE USING $N_2O_5$

A mixture of 50 ml of dried toluene and 20 g. of H-ZSM-5 was placed in a three neck 250 ml flask, stirred and heated to 110° C. The $N_2O_5$ (0.010 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 70–75° C. At the conclusion of the experiment the flask was cooled to the touch and the catalyst and solution were separated by filtration through a sintered glass funnel with medium porosity. The volatile components, primarily toluene and methylene chloride, were removed from filtrate under reduced pressure. The remaining residue is a slurry of well defined crystals that are essentially mononitrotoluenes in the amount of 0.76 g., which corresponds to a yield of 58%. The ratio of isomers for the mononitrotoluenes was 95% para, 5% ortho and trace amounts of meta (0.01%).

EXAMPLE D NITRATION OF TOLUENE USING $N_2O_5$

A mixture of 50 ml of dried toluene and 30 g. of H-ZMS-5 was placed in a three neck 250 ml flask, stirred and heated to 70° C. The $N_2O_5$ (0.010 mol.) and methylene chloride solution was decanted into an addition funnel and the solution added to the heated mixture dropwise over a 10 minute period. The original mixture was light tan and became an orange color as the reaction proceeded. The mixture was stirred for 4 hours and the temperature was kept between 105–110° C. At the conclusion of the experiment the flask was cooled to touch and the catalyst and solution was separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 1.10 g. or 80%. The ratio of isomers for the mononitrotoluenes was 96% para, 4% ortho, and trace amounts of meta (0.01%).

EXAMPLE E NITRATION OF TOLUENE USING $N_2O_5$

A mixture of 50 ml of dried toluene and 35g. of H-ZSM-5 was placed in a three neck 250 ml flask, stirred and heated to 70° C. The $N_2O_5$ (0.010 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 70–75° C. At the conclusion of the experiment the flask was cooled to touch and the catalyst and solution was separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 1.15 g. or 84%. The ratio of isomers for the mononitrotoluenes was 96% para, 4% ortho, and 0% meta.

EXAMPLE F NITRATION OF TOLUENE USING $N_2O_5$

A mixture of 50 ml of dried toluene and 35g. of H-ZMS-5 was placed in a three neck 250 ml flask, stirred and heated to 110° C. The $N_2O_5$ (0.0096 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 105–110° C. At the conclusion of the experiment the flask was cooled to touch and the catalyst and solution were separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 1.25 g. on a yield of 95%. The ratio of isomers was 96% para, 4% ortho, and 0% meta.

EXAMPLE G NITRATION OF TOLUENE USING $N_2O_5$

A mixture of 50 ml of dried toluene and 40 g. of H-ZSM-5 was placed in a three neck 250 ml flask, stirred and heated to 70° C. The $N_2O_5$ (0.010 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 70–75° C. At the conclusion of the experiment the flask was cooled to touch and the catalyst and solution was separated by filtration through a sintered glass funnel with medium porosity. The volatile components, primarily toluene and methylene chloride, were removed from the filtration under reduced pressure. The remaining residue is a slurry of well defined crystals that are essentially mononitrotoluenes in the amount of 1.20 g. or 88%. The ratio of isomers for the mononitrotoluenes was 97% para, 3% ortho, and 0% meta.

EXAMPLE H NITRATION OF TOLUENE USING $N_2O_5$

A mixture of 50 ml of dried toluene and 40 g. of H-ZMS-5 was placed in a three neck 250 ml flask, stirred and heated to 900C. The $N_2O_5$ (0.010 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 105–110° C. At the conclusion of the experiment the flask was cooled to touch and the catalyst and solution was separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 1.30 g. or 95%. The ratio of isomers for the mononitrotoluenes was 98% para, 2% ortho, and 0% meta.

EXAMPLE I NITRATION OF TOLUENE USING $N_2O_5$

A mixture of 100 ml of dried toluene and 60 g. of H-ZMS-5 was placed in a three neck 500 ml flask, stirred and heated to 90° C. The $N_2O_5$ (0.017 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 105–110° C. At the conclusion of the experiment the flask was cooled to touch and the catalyst and solution were separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 2.20 g. or 96%. The ratio of isomers for the mononitrotoluenes was 96% para, 4% ortho, and 0% meta.

EXAMPLE J NITRATION OF TOLUENE USING $N_2O_5$

A mixture of 150 ml of dried toluene and 90 g. of H-ZSM-5 was placed in a three neck 1000 ml flask, stirred and heated to 90° C. The $N_2O_5$ (0.028 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 105–110° C. At the conclusion of the experiment the flask was cooled to touch and the catalyst and solution were separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 3.40 g. or 90%. The ratio of isomers for the mononitrotoluenes was 96% para, 4% ortho, and 0% meta.

EXAMPLE K NITRATION OF TOLUENE USING $N_2O_5$

A mixture of 200 ml of dried toluene and 120 g. of H-ZMS-5 was placed in a three neck 1000 ml flask, stirred and heated to 90° C. The $N_2O_5$ (0.034 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 105–110° C. At the conclusion of the experiment the flask was cooled to touch and the catalyst and solution were separated by filtration through a sintered glass funnel with medium porosity. The volatile components, primarily toluene and methylene chloride, were removed from the filtrate under reduced pressure. The remaining residue is a slurry of well defined crystals that are essentially mononitrotoluenes in the amount of 4.36 g. or 94%. The ratio of isomers for the mononitrotoluenes was 94% para, 6% ortho, and 0% meta.

EXAMPLE L NITRATION OF TOLUENE USING $N_2O_5$

A mixture of 1 g. (0.011 mol.) of dried toluene, 50 ml of dried chloroform and 25 g. of H-ZSM-5 was placed in a three neck 250 ml flask, stirred and heated to 90° C. The $N_2O_5$ (0.0080 mol.) and methylene chloride solution was decanted into an addition funnel and the solution added to the heated mixture dropwise over a 10 minute period. The original mixture was light tan and became a orange color as the reaction proceeded. The mixture was stirred for 4 hours and the temperature was kept between 95–100° C. At the conclusion of the experiment the flask was cooled to touch and the catalyst and solution was separated by filtration through a sintered glass funnel with medium porosity. The volatile components, primarily toluene, chloroform and methylene chloride, were removed from the filtrate under reduced pressure. The remaining residue is a slurry of well defined crystals that are essentially mononitrotoluenes in the amount of 0.30 g. or 30%. The ratio of isomers for the mononitrotoluenes was 88.% para, 12% ortho, and <0.4% meta.

EXAMPLE M NITRATION OF TOLUENE USING $N_2O_5$

A mixture of 1 g. (0.011 mol.) of dried toluene, 50 ml of dried chloroform and 25 g. of R-ZSM-5 was placed in a three neck 250 ml flask, stirred and heated to 90° C. The $N_2O_5$ (0.0089 mol.) and methylene chloride solution was decanted into an addition funnel and the solution added to the heated mixture dropwise over a 10 minute period. The original mixture was light tan and became a orange color as the reaction proceeded. The mixture was stirred for 18 hours and the temperature was kept between 96–100° C. At the conclusion of the experiment the flask was cooled to touch and the catalyst and solution was separated by filtration through a sintered glass funnel with medium porosity. The volatile components, primarily toluene, chloroform and methylene chloride, were removed from the filtrate under reduced pressure. The remaining residue is a slurry of well defined crystals that are essentially mononitrotoluenes in the amount of 1.2 g. or near quantitative yield. The ratio of isomers for the mononitrotoluenes was 84.% para, 15% ortho, and 1% meta.

EXAMPLE N NITRATION OF ETHYLBENZENE USING $N_2O_5$

A mixture of 45 ml of anhydrous grade ethylbenzene and 30 g. of H-ZSM-5 was placed in a three neck 250 ml flask, stirred and heated to 90° C. The $N_2O_5$ (0.0090 mol.) solution was decanted into an addition funnel and the solution added to the heated mixture dropwise over a 10 minute period. The original mixture was light tan and became a orange color as the reaction proceeded. The mixture was stirred for 4 hours and the temperature was kept between 95–100° C. At the conclusion of the experiment the flask was cooled to touch and the catalyst and solution were separated by filtration through a sintered glass funnel with medium porosity. The volatile components, primarily ethylbenzene, chloroform and methylene chloride, were removed from the filtrate under reduced pressure. The remaining residue oil is essentially ethylnitrobenzene in the amount of 0.8 g or 59% yield.

EXAMPLE O NITRATION OF 4-PHENYLBUTYRIC ACID USING $N_2O_5$

A 0.75 g. (0.0047 mol.) of 4-phenylbutyric acid was dissolved in 60 ml of dried chloroform. This solution was then added to a three neck 250 ml roundbottom containing 30 g. of H-ZSM-5. The mixture was stirred and heated to 90° C. The $N_2O_5$ (0.011 mol.) and methylene chloride solution was decanted into an addition funnel and the solution added to the heated mixture dropwise over a 10 minute period. The original mixture was light tan and became a brown color as the reaction proceeded The mixture was stirred for 20 hours and the temperature was kept between 95–100° C. At the conclusion of the experiment the flask was cooled to touch and the catalyst and solution was separated by filtration through a sintered glass funnel with medium porosity. The volatile components, primarily chloroform and methylene chloride, were removed from the filtrate under reduced pressure. The remaining residue oil was evaluated by 1HNMR spectroscopy and determined to contain exclusively 4-(4-nitrophenyl) butyric acid in 50% yield. The other compound is the starting material.

EXAMPLE P NITRATION OF ANISOLE USING $N_2O_5$

A mixture of 40 ml of anhydrous grade anisole and 30 g. of H-ZSM-5 00 was placed in a three neck 250 ml flask, stirred and heated to 90° C. The $N_2O_5$ (0.0086 mol.) and methylene chloride solution was decanted into an addition funnel and the solution added to the heated mixture dropwise over a 10 minute period. The original mixture was light tan and became an orange color as the reaction proceeded. The mixture was stirred for 4 hours and the temperature was kept between 95–100° C. At the conclusion of the experiment the flask was cooled to touch and the catalyst and solution were separated by filtration through s sintered glass funnel with medium porosity. The volatile components, primarily anisole and methylene chloride, were removed from the filtrate under reduced pressure. The remaining residue oil is essentially p-methoxynitrobenzene in the amount of 1.08 g. or 82% yield.

While particular embodiments of the present invention have been illustrated and specifically described in this specification, it is intended that this invention includes those variations in materials, apparatus and reaction conditions as would be within the skill of the field to which it is directed.

We claim:

1. In a method for nitration of substituted aromatic compounds having at least one ring activating, ortho and para directing substituent group and where the nitration is conducted in the presence of a solid, acidic, aluminosilicate zeolite catalyst having a pore size in the range of about 5 to 5.5 Angstroms and a Si/Al ratio in the range of about 120 to about 1000, the improvement comprising reacting the aromatic compound with dinitrogen pentoxide as the nitrating agent to produce a reaction product having a high proportion of para substituted mononitro aromatics.

2. The method of claim 1 wherein the aromatic compound has at least one ortho and para directing group selected from the class consisting of alkyls, substituted alkyls, ethers, acids, oxyacids, alkoxides and halogens.

3. The method of claim 1 wherein the reaction temperature is in the range of about 40 degrees C to about 116 degrees C.

4. The method of claim 1 wherein the reaction temperature is in the range of about 90 degrees C to about 116 degrees C.

5. The method of claim 2 wherein the substituted aromatic compound is an alkyl aromatic.

6. The method of claim 2 wherein the substituted aromatic compound is toluene and the reaction product consists essentially of para nitrotoluene.

7. The method of claim 2 wherein the substituted aromatic compound is selected from alkoxy aromatic compounds and acyloxy aromatic compounds and the reaction products consist essentially of para nitro isomers of said compounds.

8. The method of claim 7 wherein the substituted aromatic compound is anisole and the reaction products consist essentially of para-nitromethoxyanisole.

9. The method of claim 7 wherein the substituted aromatic compound is 4-phenyl butyric acid and the reaction product consists essentially of 4-(4-nitrophenyl)butyric acid.

10. The method of claim 2 wherein the substituted aromatic compound is a nalobenzene.

11. The method of claim 10 wherein the substituted aromatic compound is chlorobenzene and the reaction products consist essentially of para-nitrochlorobenzene.

12. The method of claim 1 wherein the pore size of the zeolite catalyst is about 5 to about 5.4 Angstroms.

* * * * *